United States Patent
Kawagishi (10) Patent No.: US 8,949,171 B2
(45) Date of Patent: Feb. 3, 2015

(54) MEDICAL DIAGNOSTIC SUPPORTING APPARATUS

(75) Inventor: Masami Kawagishi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 443 days.

(21) Appl. No.: 12/973,780

(22) Filed: Dec. 20, 2010

(65) Prior Publication Data
US 2011/0161278 A1 Jun. 30, 2011

(30) Foreign Application Priority Data
Dec. 25, 2009 (JP) ................................. 2009-295647

(51) Int. Cl.
| | |
|---|---|
| *G06F 9/44* | (2006.01) |
| *G06N 7/02* | (2006.01) |
| *G06N 7/06* | (2006.01) |
| *G06N 7/00* | (2006.01) |
| *G06F 19/00* | (2011.01) |

(52) U.S. Cl.
CPC .............. *G06N 7/005* (2013.01); *G06F 19/321* (2013.01); *G06F 19/345* (2013.01)
USPC .......................................................... 706/52

(58) Field of Classification Search
USPC .......................................................... 706/52
See application file for complete search history.

(56) References Cited

U.S. PATENT DOCUMENTS

| 5,805,160 A | 9/1998 | Yoshida et al. |
| 5,878,746 A * | 3/1999 | Lemelson et al. ............ 600/407 |
| 6,067,466 A * | 5/2000 | Selker et al. .................. 600/513 |
| 2003/0065535 A1* | 4/2003 | Karlov et al. ..................... 705/2 |
| 2010/0256991 A1* | 10/2010 | Ishikawa et al. .................. 705/3 |
| 2010/0332441 A1* | 12/2010 | Kawagishi et al. ............ 706/52 |

FOREIGN PATENT DOCUMENTS

JP 3226400 B2 11/2001

* cited by examiner

Primary Examiner — Wilbert L Starks
Assistant Examiner — Ababacar Seck
(74) Attorney, Agent, or Firm — Canon USA Inc. IP Division (57) ABSTRACT

A medical diagnostic supporting apparatus inputs a medical image to be a target of a medical diagnosis, acquires one or more pieces of medical information relating to the medical image as entered information, and acquires an image feature amount from the medical image. The medical diagnostic supporting apparatus selects a plurality of pieces of not-entered information associated with the acquired image feature amount from not-entered information that is medical information other than the entered information as presented not-entered information candidates that are candidates for presentation, and selects presented not-entered information from the presented not-entered information candidates based on a plurality of inference results acquired using the entered information and each of the presented not-entered information candidates. The medical diagnostic supporting apparatus presents the selected presented not-entered information to a doctor.

22 Claims, 6 Drawing Sheets

MEDICAL DIAGNOSTIC SUPPORTING APPARATUS

BACKGROUND OF THE INVENTION

1. Field of the Invention

The present invention relates to a technique and a system for providing computerized information which supports a medical diagnosis.

2. Description of the Related Art

In the medical field, a medical practitioner (e.g., a doctor) observes the state of a lesioned part and a temporal change in the lesioned part by displaying a medical image obtained by capturing an image of a patient (or part thereof) on a monitor and interpreting the medical image displayed on the monitor. Examples of apparatuses generating such kind of medical images include an X-ray computed tomography (CT) apparatus, a magnetic resonance imaging (MRI) apparatus, and an ultrasonic apparatus.

A diagnosis (image diagnosis) using these medical images can be divided into the process of discovering, for example, an abnormal shadow from a medical image and obtaining the characteristics thereof, and the process of conducting a differential diagnosis to determine what the shadow is.

Conventionally, with the aim of supporting a differential diagnosis by a doctor, there has been developed a medical diagnostic supporting apparatus that infers and provides what an abnormal shadow is, based on entered information such as the characteristics of the abnormal shadow (observation from image interpretation). For example, there has been proposed an apparatus for calculating the probability that a certain shadow in a chest X-ray CT image indicates a malignant tumor and the probability that the shadow indicates a benign tumor, and presenting them.

Normally, the appropriate procedure for using such an apparatus in an actual clinical practice is as follows; first, a doctor conducts a differential diagnosis, and after that, the doctor refers to the inference result output from the medical diagnostic supporting apparatus as reference information.

One issue arising in this case is that, if there are a number of pieces of information that are not entered, the accuracy of inference by the medical diagnostic supporting apparatus is reduced. Therefore, an attempt has been made to obtain a more reliable inference result by configuring the apparatus to select not-entered information required for an inference and prompt a doctor to additionally enter that information.

Japanese Patent No. 3226400 discusses a technique of selecting and presenting noteworthy not-entered information from an inference result (current inference result) of the apparatus based on information that has been entered (entered information) and an inference result that would be produced if the information that is currently not entered is added to the entered information. This technique calculates a degree of influence that each not-entered information has on the current inference result, and presents not-entered information that has a high influence degree.

Further, Japanese Patent No. 3226400 discusses, as a method of calculating a degree of influence, the method of focusing the diagnosis name that has the highest probability in the current inference result, and using a change amount of the probability when not-entered information is added thereto as the degree of influence.

Further, Japanese Patent No. 3226400 discusses the method of focusing on the probabilities of the diagnosis names in the current inference result, and using the sum of the change amounts of the probabilities when not-entered information is added thereto as the degree of influence. In the technique discussed in Japanese Patent No. 3226400, it is thereby possible to present not-entered information that has a high influence on the inference result of the apparatus based on entered information.

However, the technique discussed in Japanese Patent No. 3226400 selects noteworthy not-entered information only based on possession of a high influence value on the inference result of the apparatus based on entered information. Therefore, sometimes, information (observation) less likely to exist in a medical image may be presented as noteworthy not-entered information.

SUMMARY OF THE INVENTION

The present invention is directed to a medical diagnostic supporting apparatus capable of efficiently presenting (e.g., displaying) information that a doctor should check preferentially.

According to an aspect of the present invention, a medical diagnostic supporting apparatus, which provides information supporting a medical diagnosis, includes a medical image input unit configured to input a medical image that is targeted by the medical diagnosis, a medical information acquisition unit configured to acquire one or more pieces of medical information with respect to the medical image as entered information, an image feature amount acquisition unit configured to acquire an image feature amount from the medical image, a presented not-entered information candidate selection unit configured to select a plurality of pieces of not-entered information associated with the image feature amount from not-entered information that is medical information other than the entered information as presented not-entered information candidates that are candidates for presentation, an inference unit configured to acquire an inference result with use of the entered information and each of the presented not-entered information candidates, a presented not-entered information selection unit configured to select presented not-entered information from the presented not-entered information candidates based on the plurality of inference result, and a presentation unit configured to present the presented not-entered information selected by the presented not-entered information selection unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
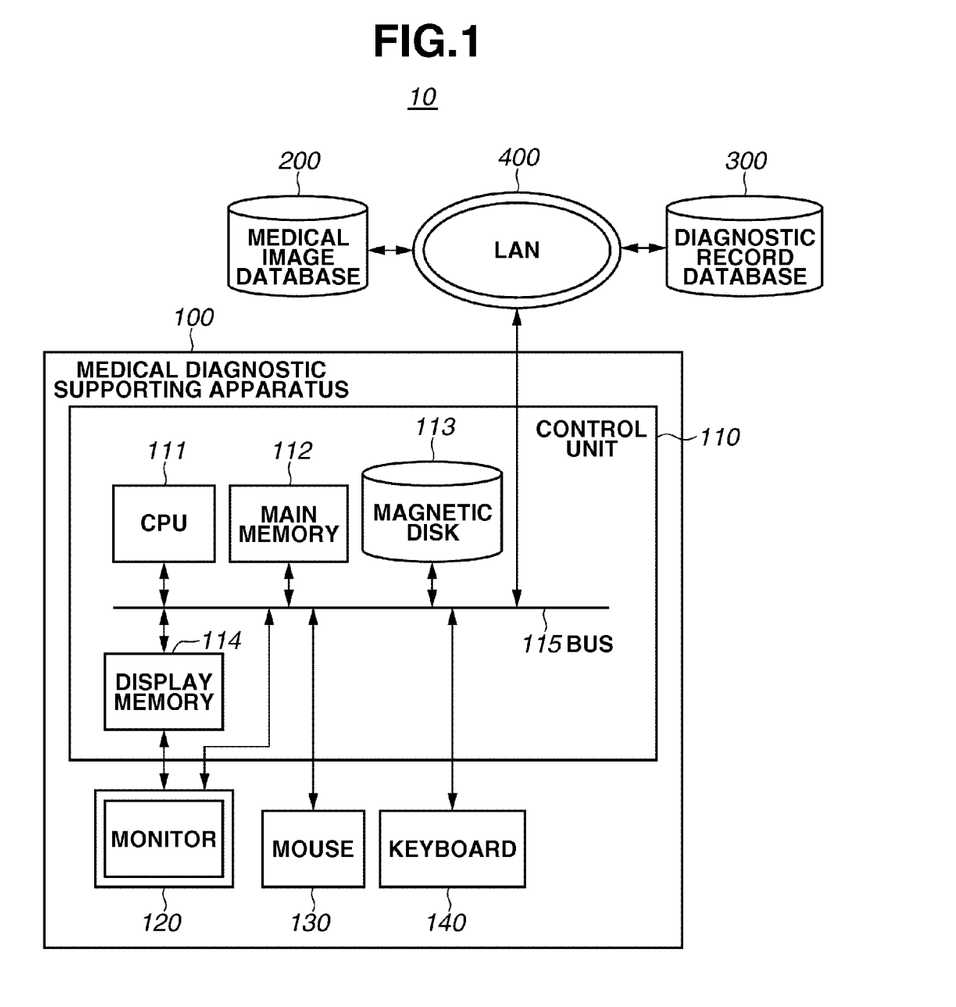
FIG. 1 schematically illustrates an example of a configuration of a medical diagnostic supporting system including a medical diagnostic supporting apparatus according to an exemplary embodiment of the present invention.

FIG. 1 schematically illustrates an example of a configuration of a medical diagnostic supporting system including a medical diagnostic supporting apparatus according to an exemplary embodiment of the present invention.

As illustrated in FIG. 1, a medical diagnostic supporting system 10 includes a medical diagnostic supporting apparatus 100, a medical image database 200, a diagnostic record database 300, and a local area network (LAN) 400. In other words, the medical diagnostic supporting system 10 illustrated in FIG. 1 is configured in such a manner that the medical diagnostic supporting apparatus 100 is connected to the medical image database 200 and the diagnostic record database 300 via the LAN 400.

The medical diagnostic supporting apparatus 100 is an apparatus for providing information which supports a medical diagnosis by, for example, a doctor. More specifically, the medical diagnostic supporting apparatus 100 is an apparatus for presenting noteworthy not-entered information (that a doctor or the like should check preferentially) by making an inference regarding a medical diagnosis based on a plurality of pieces of medical information that have been entered.

The medical diagnostic supporting apparatus 100 includes a control unit 110, a monitor 120, a mouse 130, and a keyboard 140.

The control unit 110 controls the operation of the medical diagnostic supporting apparatus 100. Control unit 110 includes a central processing unit (CPU) 111, a main memory 112, a magnetic disk 113 and a display memory 114, which are operatively interconnected to each other via a bus 115. The CPU 111 executes a program stored in, for example, the main memory 112, which realizes various controls such as communication with the medical image database 200 and the diagnostic record database 300, and overall control of the medical diagnostic supporting apparatus 100.

Mainly, the CPU 111 controls the operations of various constituent components of the medical diagnostic supporting apparatus 100, and comprehensively controls the operation of the medical diagnostic supporting apparatus 100. The main memory 112 stores the control program to be executed by the CPU 111, and provides a work area when the CPU 111 executes a program.

The magnetic disk 113 stores, for example, an operating system (OS), device drivers for peripheral devices, various kinds of application software, and work data generated or used by, for example, the various kinds of application software. The display memory 114 temporarily stores display data to be displayed on the monitor 120.

The bus 115 communicably connects the various constituent components of the medical diagnostic supporting apparatus 100 to each other, and communicably connects the medical diagnostic supporting apparatus 100 and the LAN 400 to each other.

The monitor 120 is constituted by, for example, a cathode-ray tube (CRT) monitor, a liquid crystal display (LCD) or the like that displays, for example, an image based on the display data of the display memory 114 according to the control of the CPU 111. Further, the execution status and the execution result of a program executed by the CPU 111 are displayed on the monitor 120 when it is necessary.

The present exemplary embodiment will be described based on an example of presenting noteworthy not-entered information or the like on the monitor 120. That is, in the present exemplary embodiment noteworthy not-entered information or the like is displayed on the monitor 120. However, the present invention is not limited thereto. For example, in other embodiments, the not-entered information or the like may be presented by being output to, for example, a printer, or may be presented by being output by an audio means or another means. Such embodiments are also within the scope of the present invention.

The mouse 130 and the keyboard 140 are members enabling a pointing input and an input of a character and the like by a user, respectively. A user (e.g., a doctor) inputs various commands (instruction/order) to the medical diagnostic supporting apparatus 100 by operating the mouse 130 and the keyboard 140.

The medical diagnostic supporting apparatus 100 according to the present exemplary embodiment can read out various kinds of image data from the medical image database 200 through the LAN 400, and can readout various kinds of diagnostic record data from the diagnostic record database 300.

As the medical image database 200, an existing Picture Archiving and Communication System (PACS) can be used. As the diagnostic record database 300, an electronic health record system, which is a subsystem of an existing Hospital Information System (HIS), can be used.

Alternatively, an external storage apparatus such as a floppy disk drive (FDD), a hard disk drive (HDD), a compact disk (CD) drive, a digital versatile disk (DVD) drive, a magnetooptic disk (MO) drive, or a ZIP drive may be connected to the medical diagnostic supporting apparatus 100, and the medical image data and the diagnostic record data may be read from the connected apparatus.

The medical image database 200 stores, for example, various kinds of medical image data captured by a medical image capturing apparatus (not shown). The medical diagnostic supporting apparatus 100 is connected to the medical image database 200 via the LAN 400, and acquires necessary medical image data therefrom. Examples of kinds of medical image for use in the present exemplary embodiment include a plain X-ray image (roentgen image), an X-ray CT image, an MRI image, a positron emission tomography (PET) image, a single photon emission computed tomography (SPECT) image, and an ultrasonic image.

The diagnostic record database 300 stores various kinds of diagnostic record data. The medical diagnostic supporting apparatus 100 is connected to the diagnostic record database 300 via the LAN 400, and acquires necessary diagnostic record data therefrom.

Various kinds of information are written in the diagnostic record for use in the present exemplary embodiment. The information includes personal information (for example, name, birth date, age, and sex) and clinical information (for example, various examination values, a chief compliant, previous medical history, and treatment history) of a patient, reference information to the medical image data of the patient stored in the medical image database 200, and information about an observation by a primary doctor. Further, when the diagnosis advances, a diagnosed name is written in this diagnostic record.

The LAN 400 communicably connects the medical diagnostic supporting apparatus 100, and the medical image database 200 and the diagnostic record database 300.

Next, a processing procedure of a method for controlling the medical diagnostic supporting apparatus 100 according to the present exemplary embodiment will be described.

Figure 2:
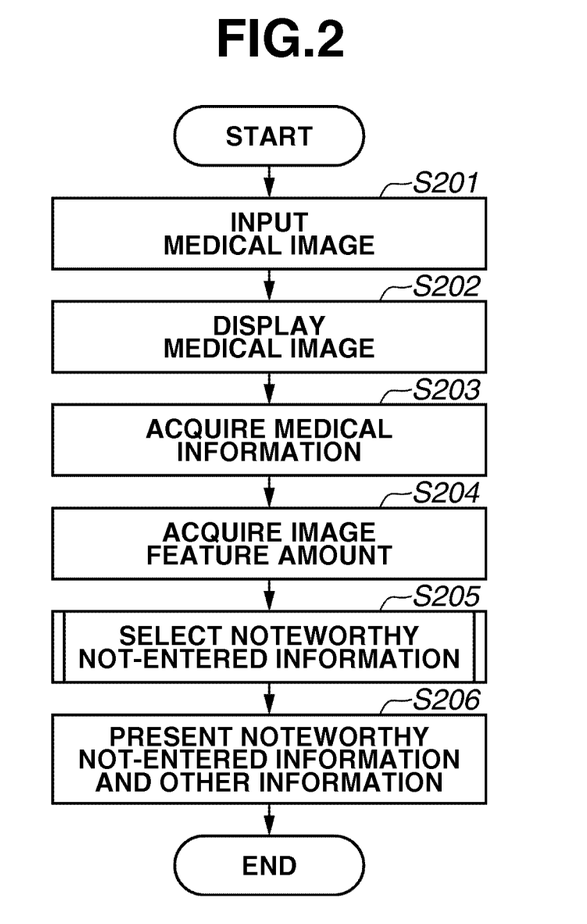
FIG. 2 is a flowchart illustrating an example of a processing procedure of a method for controlling the medical diagnostic supporting apparatus according to the exemplary embodiment of the present invention.

FIG. 2 is a flowchart illustrating an example of the processing procedure of the method for controlling the medical diagnostic supporting apparatus 100 according to the exemplary embodiment of the present invention. In particular, the CPU 111 executes the program stored in the main memory 112, which realizes the flowchart illustrated in FIG. 2.

Figure 3:
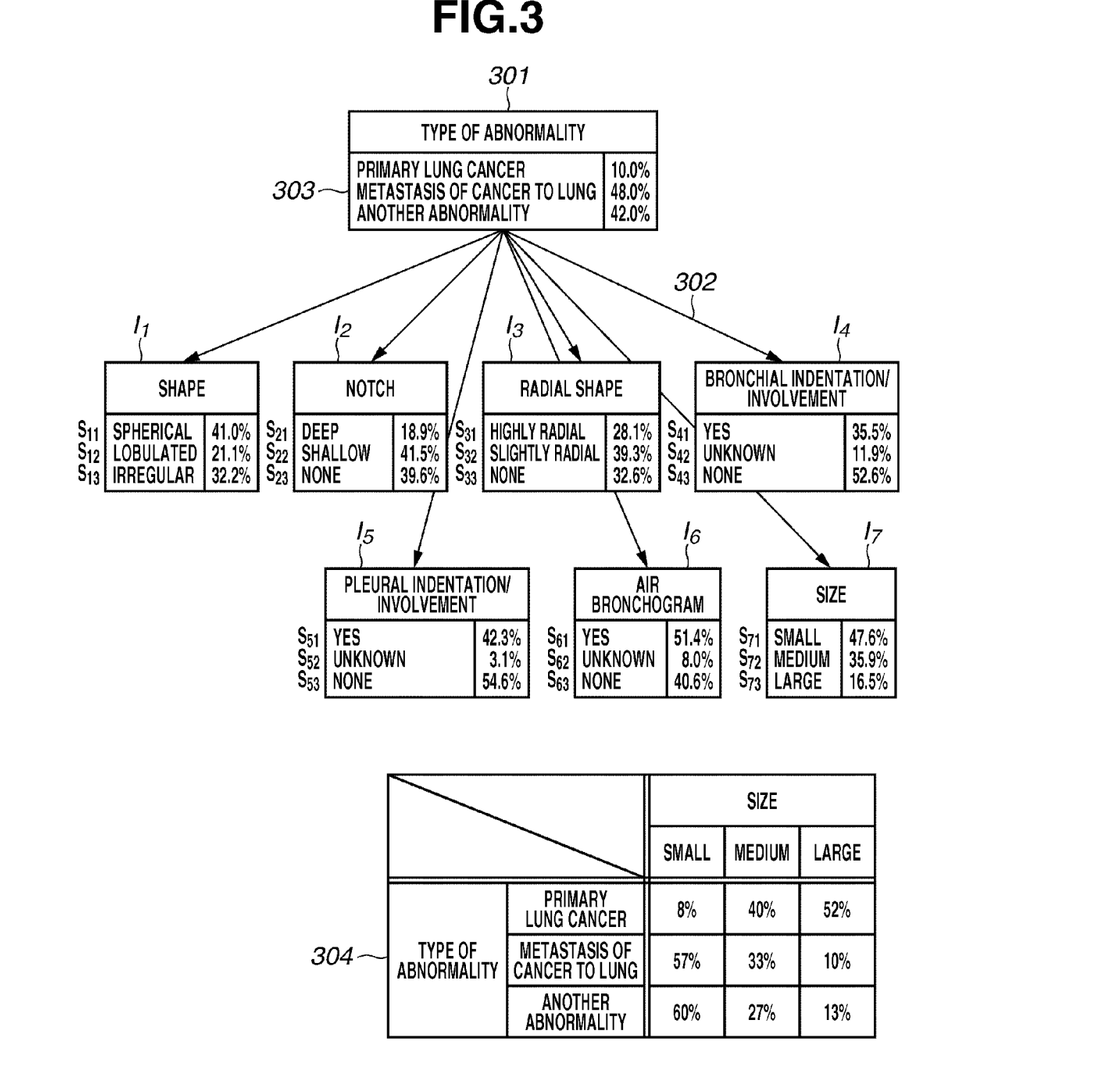
FIG. 3 illustrates a typical example of a probabilistic inference model with use of a Bayesian network according to the exemplary embodiment of the present invention.

Further, FIG. 3 illustrates an example of a probabilistic inference model with use of a Bayesian network according to the present exemplary embodiment.

In the following description, a case where supporting of a medical diagnosis of an abnormal shadow in a lung is performed by using the medical diagnostic supporting apparatus 100 is described as an example. It should be noted that an inference target is not limited thereto, and options of diagnosis name and enterable medical information therefor which will be described below are all just an example for facilitating understanding of the steps of the processing by the medical diagnostic supporting apparatus 100.

Further, in the following description, options for diagnosis name (types of abnormality) handled by the medical diagnostic supporting apparatus 100 will be denoted with use of character "D". More specifically, the present exemplary embodiment handles "primary lung cancer", "metastasis of cancer to lung", and "another abnormality" illustrated in a state 303 in FIG. 3 as options for diagnosis name, which will be denoted as "$D_1$", "$D_2$", and "$D_3$", respectively in the following description.

Further, in the following description, the medical information handled by the medical diagnostic supporting apparatus 100 will be denoted as "Ij". More specifically, the present exemplary embodiment handles seven types of medical information $I_1$ to $I_2$ illustrated in FIG. 3. For example, medical information $I_1$ "shape" illustrated in FIG. 3 indicates what kind of shape an abnormal shadow has. Further, medical information $I_5$ "pleural indentation/involvement" illustrated in FIG. 3 indicates whether there is pleural indentation/involvement in the organ.

Further, in the following description, possible states (discrete values) for each medical information "Ij" will be denoted as "Sjk". The range of k varies depending on "Ij". In the present exemplary embodiment, as illustrated in FIG. 3, for example, medical information $I_1$ "shape" has three possible states, $S_{11}$ "shape—spherical", $S_{12}$ "shape—lobulated", and $S_{13}$ "shape—irregular".

Further, in the following description, a group of "Ij" will be denoted with use of character "N", and a group of "Sjk" will be denoted with use of character "C" or "E".

Character "C" is used to denote a plain group of "Sjk". For example, a group constituted by $S_{11}$, $S_{12}$, and $S_{51}$ as elements is expressed as C={$S_{11}$, $S_{12}$, $S_{51}$}. In the example illustrated in FIG. 3, this group is C={shape—spherical, shape—lobulated, pleural indentation/involvement—yes}.

On the other hand, character "E" is used to denote a settable group of "Sjk". The term "settable" here means that "Sjk" cannot exist simultaneously for each "Ij" in a single "E". Similar to the above-described example, if there are $S_{11}$, $S_{12}$, and $S_{51}$ as elements, {$S_{11}$, $S_{51}$} can occur, but {$S_{11}$, $S_{12}$} never occurs. This is because one type of medical information can have only one state. In the example illustrated in FIG. 3, the group {shape—spherical, pleural indentation/involvement—yes} can occur, but the group {shape—spherical, shape—lobulated} never occurs.

First, in step S201 in FIG. 2, the CPU 111 performs input processing of desired medical image data from the medical image database 200 to the medical diagnostic supporting apparatus 100 in response to an input to the mouse 130 and the keyboard 140 (medical image input process).

Hereinafter, the medical image data input in step S201 will be referred to as "interpretation target image". As mentioned above, this interpretation target image data input processing is carried out by the CPU 111 receiving desired medical image data as an interpretation target image through the LAN 400 from the medical image database 200 storing captured medical image data.

The processing of step S201 may be realized by the CPU 111 reading out desired medical image data as an interpretation target image from any storage medium connected to the medical diagnostic supporting apparatus 100, such as a FDD, a CD-rewritable (CD-RW) drive, an MO (magneto-optical) drive, and a ZIP drive.

Next, in step S202, the CPU 111 displays, on the monitor 120, the interpretation target image input into the medical diagnostic supporting apparatus 100 in step S201.

In step S203, the CPU 111 acquires, as medical information, an observation from shadow interpretation that a doctor inputs with user of, for example, the mouse 130 and the keyboard 140 while viewing the interpretation target image displayed on the monitor 120 (medical information acquisition process).

This processing of step S203 is realized by, for example, providing the medical diagnostic supporting apparatus 100 with such a function that a doctor can select any one of the corresponding states Sjk for the respective types of medical information Ij by using a template-based interpretation observation input supporting method.

In the following description, a group of medical information Ij acquired in step S203 will be denoted as "Nf", and a group of states Sjk thereof will be denoted as "Ef". These pieces of information will be referred to as "entered information".

For example, it is assumed that the medical information acquired in step S203 is $S_{11}$ "shape—spherical", $S_{33}$ "radial shape—none", $S_{41}$ "bronchial indentation/involvement—yes", $S_{53}$ "pleural indentation/involvement—yes", and $S_{71}$ "size—small" illustrated in FIG. 3. In this case, {$I_1$, $I_3$, $I_4$, $I_5$, $I_7$} is acquired as the entered information Nf, and {$S_{11}$, $S_{33}$, $S_{41}$, $S_{53}$, $S_{71}$} is acquired as the entered information Ef.

If there are a plurality of tumor masses in the interpretation target image, a doctor should identify which tumor mass the doctor interprets (which tumor mass the doctor inputs an observation for) by some method.

For example, this can be realized by the doctor specifying the location of the tumor mass by using the mouse 130 on the interpretation target image displayed on the monitor 120. The location of the tumor mass may be specified by, for example, clicking the center of the tumor mass or specifying a rectangular area surrounding the tumor mass.

Next, in step S204, the CPU 111 performs image processing on the interpretation target image input in step S201, and acquires various image feature amounts regarding the tumor mass that the doctor has specified as an interpretation target by, for example, the mouse 130 in step S203 (image feature amount acquisition process).

More specifically, in the processing of step S204, the following information is acquired as image feature amounts. First, the area of the tumor mass specified as the interpretation target is extracted by binarization processing, and the degree of irregularity of the periphery is calculated based on the degree of coincidence of the area obtained by applying distance conversion to the area and inversely converting only pixels having the maximum value (for the details thereof, refer to, for example, "Classification of tumors in chest X-ray CT images into the solid and air-containing type and its application to discrimination of the benign and malignant tumors" written by Kondo, et al, published in the Institute of Electronics, Information and Communication Engineers (IEICE) technical report MI2000-16, May 2000).

Further, after the area of the tumor mass specified as the interpretation target is extracted, the distances from the respective points on the periphery to the centroid of the area, and the variance thereof are calculated. Further, the bronchus is extracted with use of, for example, the method described in "Bronchial wall regions extraction algorithm using multi slice CT images" written by Tada, et al, published in the IEICE technical report MI2004-37, September 2004, and it is determined whether the bronchus exists within the tumor mass. Further, if it is determined that the bronchus exists in the tumor mass, it is determined whether there is an annular structure of air based on the internal density of the tumor mass. In addition, the maximum diameter of the tumor mass is calculated.

It should be noted that these image feature amounts are mere an example for facilitating understanding of image feature amount in the present exemplary embodiment, and image feature amounts to be acquired are not limited thereto.

Further, since the image feature amounts acquired in step S204 are used to narrow down not-entered information, only image feature amounts having an influence on not-entered information may be acquired. In other words, the processing for acquiring image feature amounts having an influence only on the entered information Nf acquired in step S203 may be omitted. For example, when $S_{71}$ "size—small" illustrated in FIG. 3 is acquired as entered information, calculation of the maximum diameter of the tumor mass may be omitted.

Next, in step S205, the CPU 111 selects not-entered information to be presented in step S206 (hereinafter referred to as "presented not-entered information") based on the medical information on the interpretation target image acquired in step S203 and the image feature amounts acquired in step S204.

In the present exemplary embodiment, the diagnosis name having the highest probability is selected as a predicted diagnosis name Df from the inference result based on the entered information Ef. Not-entered information Eh, which is the not-entered information most affirming the predicted diagnosis name Df, and not-entered information El, which is the not-entered information most denying the predicted diagnosis name Df, are estimated, and selected as presented not-entered information.

Figure 4:
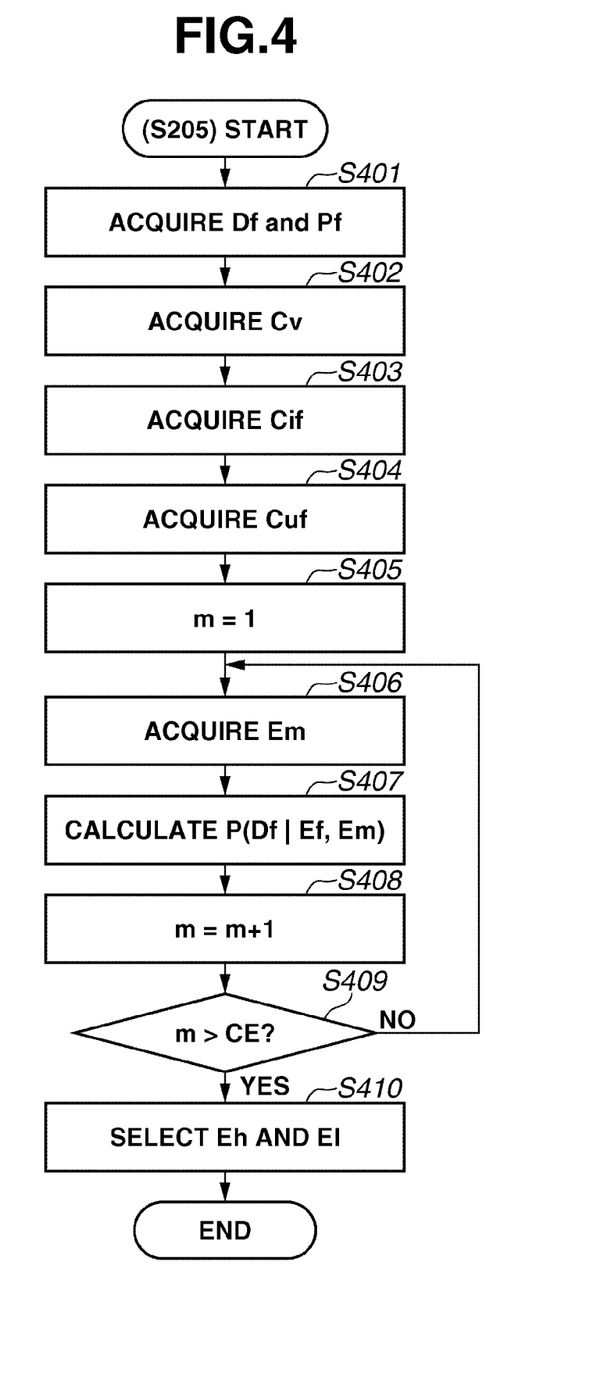
FIG. 4 is a flowchart illustrating an example of a detailed processing procedure performed in step S205 illustrated in FIG. 2.

Now, the processing procedure performed in step S205 illustrated in FIG. 2 will be described in detail. FIG. 4 is a flowchart illustrating an example of the detailed processing procedure performed in step S205 illustrated in FIG. 2.

Upon a start of the processing of step S205 illustrated in FIG. 2, first, in step S401 in FIG. 4, the CPU 111 calculates and acquires the probability P (Di|Ef) belonging to each diagnosis name Di (i=1 to 3) based on the entered information Ef as an input with use of the probabilistic inference model.

At this time, the CPU 111 stores the Di having the highest probability in the probabilities P (Di|Ef) as the predicted diagnosis name Df into the main memory 112, and also stores this probability P (Di|Ef) (hereinafter denoted as "Pf") into the main memory 112.

In the following description, an example the case is described where the highest probability Pf=66.2% is acquired for the diagnosis name $D_2$ "metastasis of cancer to lung" in an inference based on the entered information Ef as an input. This calculation of the inferred probability Pf corresponds to a second inference process in the present exemplary embodiment, and the acquired inferred probability Pf corresponds to a second inference result in the present exemplary embodiment.

There are various methods as an inference model for performing the inference processing of calculating the inferred probability belonging to a currently focused diagnosis name with use of entered information. As an example thereof, the present exemplary embodiment employs the Bayesian network as illustrated in FIG. 3. It should be noted that the following method is mere an example of the inference model, and the inference method, the structure of the inference model, and the like are not limited thereto.

The Bayesian network illustrated in FIG. 3 is a model expressing a phenomenon by a causal relationship between a plurality of events. In the Bayesian network illustrated in FIG. 3, a relationship between events is expressed by a probability, and an event constituting the target phenomenon is expressed as a node 301, and a relationship between nodes is expressed as a link 302.

As illustrated in FIG. 3, the links 302 are indicated by arrows. The node at the roots of the arrows is referred to as "parent node", and the nodes at the tips of the arrows are referred to as "child nodes". Each node has a plurality of states 303 indicating states of the node. An occurrence probability (referred to as "prior probability") is assigned to each state. The relationship between the parent node and the child node is determined based on a conditional probability in which the parent node is set as a condition. The table containing this conditional probability is referred to as a conditional probability table (CPT).

The CPT 304 illustrated in FIG. 3 is an example of the CPT between the parent node 301 and the node $I_7$ which is a child node. Further, information indicating what states (for example, state 303) of at least one node of a target model are, is referred to as "evidence". The probability (referred to as "posterior probability") of a desired node can be acquired based on this evidence, the CPT 304, and the Bayes' theorem by the belief propagation method.

Returning to FIG. 4, upon a completion of the processing of step S401, the processing proceeds to step S402. In step S402, the CPU 111 acquires a group of the states belonging to all pieces of enterable medical information except for the entered information Nf (other than the entered information), i.e., a group (hereinafter denoted as "Cv") of the states of the not-entered medical information.

For example, in the example illustrated in FIG. 3, if the entered information Nf is $\{I_1, I_3, I_4, I_5, I_7\}$, a group constituted by the states of medical information $I_2$ and $I_6$ $\{S_{21}, S_{22}, S_{23}, S_{61}, S_{62}, S_{63}\}$ is acquired as "Cv".

Next, in step S403, the CPU 111 acquires a group (hereinafter denoted as "Cif") constituted by the states of the medical information corresponding to the image feature amounts based on the image feature amounts acquired in step S204.

For example, the state of $I_1$ "shape" illustrated in FIG. 3 is selected with use of the degree of irregularity of the periphery which is one of the image feature amounts. For example, if it is determined that the degree of irregularity of the periphery is high (equal to or higher than a predetermined threshold value), $S_{12}$ {shape—lobulated} and $S_{13}$ {shape—irregular} are selected to be included in the elements of "Cif" as possible corresponding states. On the contrary, if it is determined that the degree of irregularity of the periphery is low (equal to or lower than the predetermined threshold value), $S_{11}$ {shape—spherical} is selected to be included in the elements of "Cif" as a possible corresponding state.

Further, the state of $I_2$ "notch" is selected based on the distance of the periphery which is one of the image feature amounts. In the following, an example of the selection method therefor will be described with reference to FIG. 5.

Figure 5:
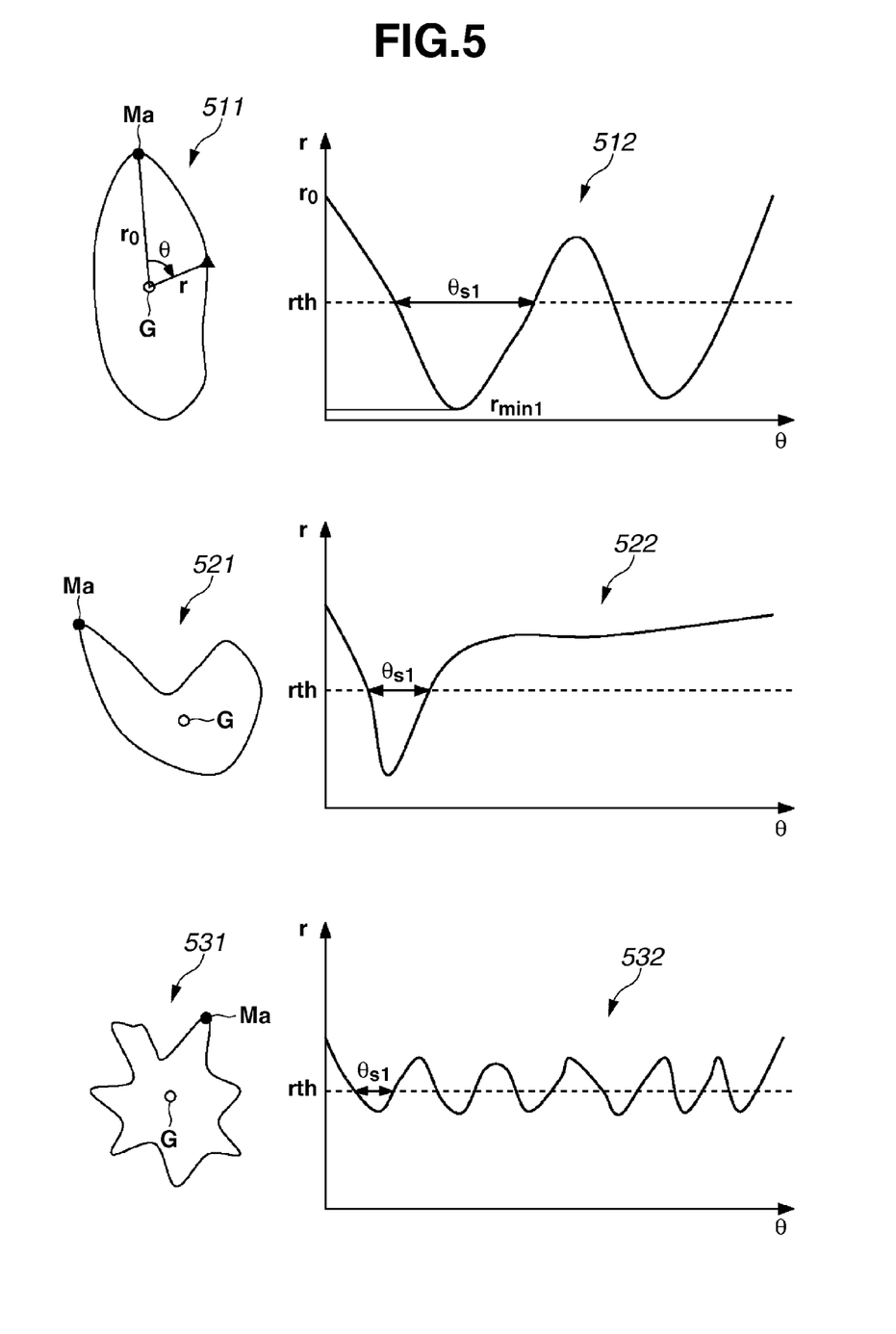
FIG. 5 illustrates the exemplary embodiment of the present invention, and in particular, illustrates an example of the relationship between the distance and angle between each point at the periphery and the centroid of the area in the form of polar coordinate in which the vertical axis represents a distance r and the horizontal axis represents an angle θ.

FIG. 5 illustrates an example of the relationship between the distance and the angle between each point at the periphery and the centroid of the area in the form of polar coordinate in which the vertical axis represents a distance r and the horizontal axis represents an angle θ, according to the present exemplary embodiment.

First, a centroid point G (white circle in FIG. 5) of each area 511 to 531, and a peripheral point Ma (black circle in FIG. 5) which has the longest distance (r0) from the centroid point G are acquired. Then, the direction (hereinafter referred to as "reference direction") of the line segment connecting these two points is acquired.

At this time, an arbitrary peripheral point can be expressed by the distance r from the centroid point G, and the angle θ defined between the line segment connecting the centroid point G and the peripheral point and the reference direction (in the clockwise direction).

Then, an angular range θsk (k>=1) of points having the distance r from the centroid point G which is equal to or shorter than a threshold value rth is acquired. Further, the minimum distance r (hereinafter referred to as "rmink") within the range θsk is acquired. If θsk is within a predetermined range and acquired once or twice, it is determined that the possibility of presence of a notch is high (although it is unclear how deep or shallow the notch is).

In the example (511 and 512) illustrated at the upper portion in FIG. 5, θsk are acquired twice, but neither of the θsk are within the predetermined range (not shown), and therefore it is determined that the possibility of presence of a notch is low. Then, $S_{22}$ {notch—shallow} and $S_{23}$ {notch—none} illustrated in FIG. 3 are selected to be included in the elements of "Cif" as possible corresponding states.

On the other hand, in the example (521 and 522) illustrated at the middle in FIG. 5, θsk is acquired once and this θsk is within the predetermined range (not shown), and therefore it is determined that the possibility of presence of a notch is high. Then, $S_{21}$ {notch—deep} and $S_{22}$ {notch—shallow} illustrated in FIG. 3 are selected to be included in the elements of "Cif" as possible corresponding states.

On the other hand, in the example (531 and 532) illustrated at the bottom in FIG. 5, θsk are acquired six times and therefore it is determined that the possibility of presence of a notch is low. Then, $S_{22}$ {notch—shallow} and $S_{23}$ {notch—none} illustrated in FIG. 3 are selected to be included in the elements of "Cif" as possible corresponding states.

Further, the state of $I_3$ "radial shape" illustrated in FIG. 3 is selected based on the variance of the distances at the periphery which is one of the image feature amounts. For example, if it is determined that the variance is large (equal to or larger than a predetermined threshold value), $S_{31}$ {radial shape—highly radial} and $S_{32}$ {radial shape—slightly radial} illustrated in FIG. 3 are selected to be included in the elements of "Cif" as possible corresponding states.

On the contrary, if it is determined that the variance is small (equal to or smaller than the predetermined threshold value), $S_{32}$ {radial shape—slightly radial} and $S_{33}$ {radial shape—none} illustrated in FIG. 3 are selected to be included in the elements "Cif" as possible corresponding states.

Similarly, the state of $I_6$ "air bronchogram" illustrated in FIG. 3 is selected (determined) based on information indicating whether the bronchus exists within the tumor mass which is one of the image feature amounts.

For example, if it is determined that the bronchus does not exist within the tumor mass, all of the states regarding air bronchogram are excluded from the elements of "Cif". For example, this is applicable to the case where a tumor mass exists at the side of a main bronchus or near a chest wall. This is because the determination is impossible without information with respect to air bronchogram in the image.

It should be noted that the state $S_{63}$ {air bronchogram—none} indicates that there is no air bronchogram when the bronchus exists within the tumor mass, and therefore indicates a different state from the above-described case.

On the other hand, if it is determined that the bronchus exists within the tumor mass, the state of $I_6$ "air bronchogram" illustrated in FIG. 3 is further determined based on the information indicating whether there is an annular structure of air within the tumor mass which is one of the image feature amounts. For example, if there is an annular structure of air within the tumor mass, the state $S_{61}$ {air bronchogram—yes} is selected to be included in the elements of "Cif" as a possible corresponding state.

On the other hand, if there is no annular structure of air within the tumor mass, since the determination is difficult for this case, all of the states $S_{61}$ {air bronchogram—yes}, $S_{62}$ {air bronchogram—unknown}, and $S_{63}$ {air bronchogram—none} are selected to be included in the elements of "Cif" as possible corresponding states.

Further, the state of $I_7$ "size" illustrated in FIG. 3 is selected (determined) based on the size of the tumor mass which is one of the image feature amounts.

If the acquired size of the tumor mass is smaller than a predetermined threshold value, the states $S_{71}$ {size—small} and $S_{72}$ {size—medium} are selected to be included in the elements of "Cif" as possible corresponding states. On the contrary, if the acquired size of the tumor mass is larger than the predetermined threshold value, the states $S_{73}$ {size—large} and $S_{72}$ {size—medium} are selected to be included in the elements of "Cif" as possible corresponding states.

Regarding the medical information that cannot be determined from the image feature amounts, all of the states thereof are selected to be included in the elements "Cif".

It should be understood that the above description is mere an example indicating the correspondence between an image feature amount and a state of medical information, and image feature amounts to be used, a method for selecting a state and the like are not limited thereto. For example, only a part of the above-described determination processing may be used.

For example, when it is determined that the bronchus does not exist within the tumor mass, only the processing of excluding all of the states regarding $I_6$ "air bronchogram" illustrated in FIG. 3 from "Cif" may be performed. Further, any image feature amount other than the image feature amounts described above may be used, and any determination processing for determining the existence possibility of a corresponding state from the image feature amount may be used.

For example, it is assumed that the following image feature amounts are acquired from the processing of step S204.

degree of irregularity of periphery: equal to or smaller than the predetermined threshold value shape of distances of periphery: no θsk is acquired variance of distances of periphery: equal to or smaller than the predetermined threshold value the bronchus exists in the tumor mass there is an annular structure of air within the tumor mass size of tumor mass: equal to or smaller than the predetermined value In this case, in step S403, $\{S_{11}, S_{22}, S_{23}, S_{32}, S_{33}, S_{41}, S_{42}, S_{43}, S_{51}, S_{52}, S_{53}, S_{61}, S_{71}, S_{72}\}$ is set as "Cif".

Returning to FIG. 4, upon a completion of the processing of step S403, the processing proceeds to step S404. In step S404, the CPU 111 determines common states existing in both "Cv" acquired in step S402 and "Cif" acquired in step S403, and acquires a group (hereinafter denoted as "Cuf") constituted by possible states of not-entered medical information.

In the above-described example, comparison of "Cv" and "Cif" to determine common states shared thereby results in the acquisition of $\{S_{22}$ "notch—shallow", $S_{23}$ "notch—none", $S_{61}$ "air bronchogram—yes"$\}$ as "Cuf". In other words, $S_{21}$ "notch—deep", $S_{62}$ "air bronchogram—unknown", and $S_{63}$ "air bronchogram—none" each are excluded from candidates for presentation as states unlikely to exist.

Next, in step S405, the CPU 111 prepares a variable m, and sets 1 to m (m=1).

Next, in step S406, the CPU 111 first selects one or more "Sjk" from "Cuf" which is a group constituted by candidates of states of not-entered medical information. Then, the CPU 111 generates (acquires) a virtual group Em of "Sjk", and sets this group as a presented not-entered information candidate (presented not-entered information candidate selection process).

In the case of m>1 (in other words, in the case of the second execution of the processing of step S406 or the execution of the processing of step S406 after that), the CPU 111 generates (acquires), as Em, a group different from the groups $E_1$ to $E_{m-1}$ that have been generated before this time. The number of "Sjk" belonging to Em may be a predetermined plural number or a number less than the plural number, or may be specified by a doctor.

In the following description, "1" is set as the number of "Sjk" as an example. For example, in the above-described example, "Cuf" is constituted by $S_{22}$ "notch—shallow", $S_{23}$ "notch—none", and $S_{63}$ "air bronchogram—yes" illustrated in FIG. 3. In this case, for example, the CPU 111 generates (acquires) $E_1$ as $\{S_{22}$ "notch—shallow"$\}$.

In step S407, the CPU 111 inputs the set of the entered information Ef and the presented not-entered information candidate Em, and calculates the probability P (Df|Ef, Em) belonging to the predicted diagnosis name Df by the inference model. Then, the CPU 111 stores the acquired inferred probability (hereinafter denoted as "Pm") in the main memory 112 in such a manner that this inferred probability is associated with the presented not-entered information candidate Em.

This calculation of the inferred probability Pm corresponds to an inference process in the present exemplary embodiment, and the acquired inferred probability Pm corresponds to an inference result in the present exemplary embodiment. For example, if the predicted diagnosis name Df is "metastasis of cancer to lung", the inferred probability belonging to "metastasis of cancer to lung" is calculated by the inference model illustrated in FIG. 3 with use of the set of Ef=$\{S_{11}, S_{33}, S_{41}, S_{53}, S_{71}\}$ and $E_1$=$\{S_{22}\}$ as an input, as a result which is 60.2%. Then, this inferred probability is stored in such a manner that this inferred probability is associated with $E_1$=$\{S_{22}\}$.

Next, in step S408, the CPU 111 adds 1 to the variable m.

Next, in step S409, the CPU 111 determines whether the processing from the step S406 to step S408 should be repeated. More specifically, in step S409, the CPU 111 determines whether the value of the valuable m is greater than the number (hereinafter denoted as "CE") of possible combinations as Em.

If it is determined as a result of the determination in step S409 that the value of the valuable m is not greater than CE (in other words, the value of the valuable m is smaller than CE) (NO in step S409), since this means that acquisition of all Pm is not yet completed, the processing returns to step S406 so that the processing of step S406 and the subsequent processing are repeated.

On the other hand, if it is determined as a result of the determination of step S409 that the value of the valuable m is greater than CE (YES in step S409), the processing proceeds to step S410. For example, in the above-described example, since the number of possible combinations of Em, i.e., CE is 3, the processing from step S406 to step S409 is repeated until $E_3$ is processed. Then, when m becomes 4, since m becomes greater than CE, the processing proceeds to step S410.

In step S410, the CPU 111 selects any of Em generated and acquired in step S406 as not-entered information that is most worthy of being presented to a doctor (presented not-entered information selection process).

More specifically, Em having the highest inferred probability Pm stored in the main memory 112 by the above-described processing is stored in the main memory 112 as not-entered information Eh that most affirms the predicted diagnosis name.

Further, the inferred probability (hereinafter denoted as "Ph") at this time is stored in the main memory 112 in such a manner that this is associated with the not-entered information Eh. Similarly, Em having the lowest inferred probability Pm is stored in the main memory 112 as not-entered information El that most denies the predicted diagnosis name. Further, the inferred probability (hereinafter denoted as "Pl") at this time is stored in the main memory 112 in such a manner that this is associated with the not-entered information El.

TABLE 1

| m | $E_m$ | P ($D_2$|$E_f$, $E_m$) |
|---|---|---|
| 1 | {NOTCH - SHALLOW} | 60.2% |
| 2 | {NOTCH - NONE} | 71.6% |
| 3 | {AIR BRONCHOGRAM - YES} | 44.1% |

P ($D_2$|$E_f$) 66.2%

The table 1 indicates an example of $E_1$ to $E_3$ and the inferred probability P (Df|Ef, Em) thereof in the above-described example. In this example, $E_2$, i.e., $S_{23}$ {notch—none} illustrated in FIG. 3 provides the highest inferred probability 71.6%, while $E_3$, i.e., $S_{61}$ {air bronchogram—yes} illustrated in FIG. 3 provide the lowest inferred probability 44.1%. Therefore, in this case, Eh=$\{S_{23}\}$ and El=$\{S_{61}\}$ are stored in the main memory 112.

After the processing of step S410 is completed, the operation according to the flowchart of FIG. 4 is ended. In this way, execution of processing of steps S401 to S410 illustrated in FIG. 4 constitutes execution of the processing of step S205 illustrated in FIG. 2.

Now, returning to FIG. 2, after the processing of step S205 is completed, the processing proceeds to step S206. In step S206, the CPU 111 displays and presents, for example, the noteworthy not-entered information (for example, presented not-entered information) selected in step S205 on the monitor 120 (presentation process). More specifically, the CPU 111 displays Eh (not-entered information affirming Df) and El (not-entered information denying Df) stored in the main memory 112 on the monitor 120.

Figure 6:
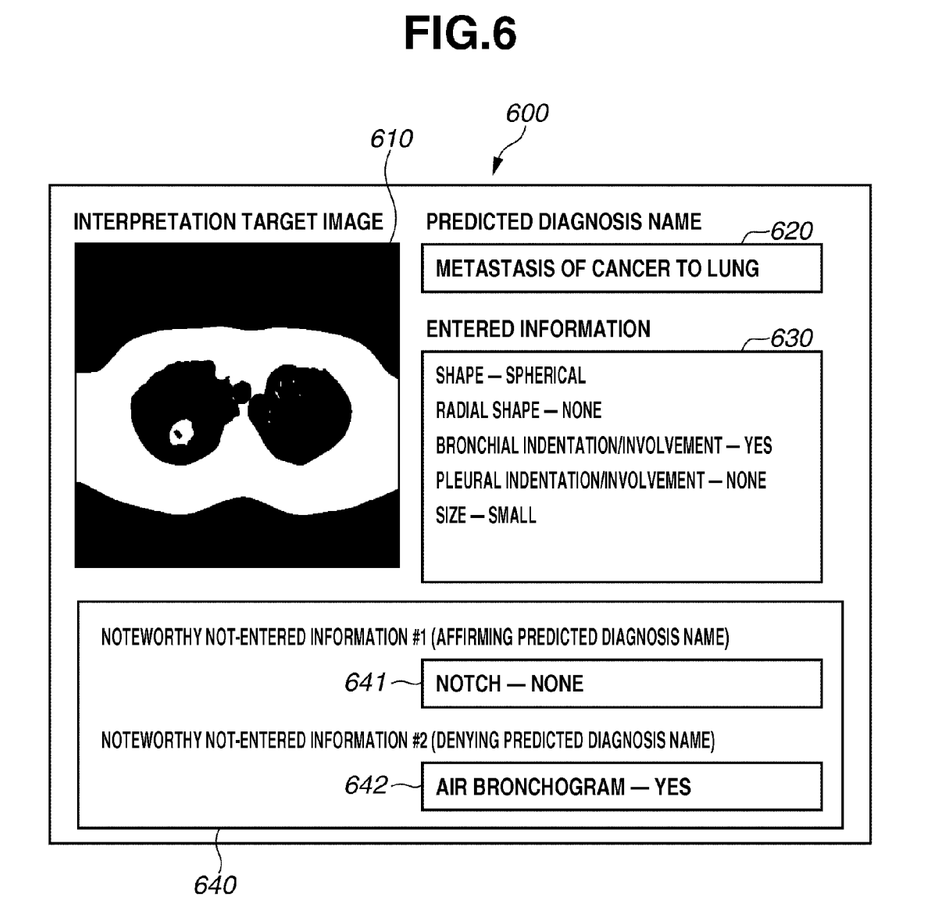
FIG. 6 illustrates an example of a monitor display screen according to the exemplary embodiment of the present invention.

FIG. 6 illustrates an example of a monitor display screen according to the present exemplary embodiment. In the example illustrated in FIG. 6, the monitor display screen 600 shows the interpretation target image 610 displayed in step S202.

Further, the monitor display screen 600 shows the predicted diagnosis name Df (metastasis of cancer to lung) acquired in step S401 at a predicted diagnosis name 620 field, the medical information (entered information) Ef acquired in step S203 at an entered information 630 field. Further, the monitor display screen 600 shows noteworthy not-entered information 640.

More specifically, the not-entered information Eh that affirms the predicted diagnosis name, i.e., "notch—none" is displayed as noteworthy not-entered information 641, and the not-entered information El that denies the predicted diagnosis name, i.e., "air bronchogram—yes" is displayed as noteworthy not-entered information 642.

Use of the medical diagnostic supporting apparatus 100 according to the present exemplary embodiment enables a doctor to recognize medical information that a doctor should check preferentially to obtain information helpful for his/her diagnosis by referring to the presented not-entered information.

The medical diagnostic supporting apparatus 100 according to the present exemplary embodiment can present not-entered information that likely exists in an interpretation target image and has an influence on a predicted diagnosis name. Due to this function, the medical diagnostic supporting apparatus 100 can present preferential medical information helpful for a diagnosis to, for example, a doctor.

Further, the medical diagnostic supporting apparatus 100 according to the present exemplary embodiment uses image feature amounts only for the purpose of excluding obviously irrelevant states from candidates for states to be presented. Therefore, unlike the processing of automatically determining an observation from image feature amounts, it is possible to realize a diagnosis support effectively using information of image feature amounts, even when it is difficult to obtain perfect accuracy of detecting the image feature amounts and reliably associate the image feature amount with states.

As mentioned above, according to the medical diagnostic supporting apparatus 100 according to the present exemplary embodiment, it is possible to efficiently present information that a doctor should check preferentially, due to selection and presentation of not-entered information that has a high influence on an inference result and is highly likely to exist.

In the above-described exemplary embodiment, the medical diagnostic supporting apparatus 100 acquires, as medical information, an observation that a doctor inputs as a result of his/her interpretation of a medical image that the medical diagnostic supporting apparatus 100 displays in step S203 in FIG. 2. However, in the present invention, the method for acquiring medical information is not limited thereto. For example, the medical diagnostic supporting apparatus 100 may set, as a processing target (entered information/not-entered information), medical information of medical examination data including, for example, a previous interpretation report, a clinical report, and other information usable for diagnosis supporting processing with respect to a person (patient) to be examined.

Further, the processing of acquiring image feature amounts performed in step S204 in FIG. 2 may be performed before step S203 in FIG. 2 or after step S402 in FIG. 2.

In the above-described exemplary embodiment, the description has been given assuming that all medical information has discrete values. However, instead, continuous values may be acquired as input information and these values may be discretized to be used.

Further, in the above-described exemplary embodiment, the medical diagnostic supporting apparatus 100 selects, as the elements of "Cif", all of the states with respect to the observations that have not been determined as to their possibilities of presence or absence based on the image feature amounts in the processing of step S403 in FIG. 4. However, the present invention is not limited thereto, and the medical diagnostic supporting apparatus 100 may be configured in such a manner that all of such states are excluded from "Cif".

Further, the presented not-entered information selected in step S205 in FIG. 2 is selected based on the diagnosis name that has the highest probability in the probabilities acquired in step S401 in FIG. 4. However, the present invention is not limited thereto.

For example, the medical diagnostic supporting apparatus 100 may be configured in such a manner that not-entered information that provides the highest (or lowest) possibility for the diagnosis name is selected for each diagnosis name ($D_1$, $D_2$, and $D_3$), and each of that not-entered information is presented while being associated with the corresponding diagnosis name.

Further, the present invention can be also embodied by performing the following procedure. That is, a software application (or program) capable of carrying out the functions of the above-described exemplary embodiment is supplied to a system or an apparatus through a network or various kinds of storage media, and a computer (or, for example, a CPU or a micro processing unit (MPU)) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-295647 filed Dec. 25, 2009, which is hereby incorporated by reference herein in its entirety.

What is claimed is:

1. A medical diagnostic supporting apparatus for providing information which supports a medical diagnosis, the medical diagnostic supporting apparatus comprising:
a medical image input unit configured to input a medical image that is a target of the medical diagnosis;
a medical information acquisition unit configured to acquire one or more pieces of medical information relating to the medical image as entered information;
an image feature amount acquisition unit configured to acquire an image feature amount from the medical image; and
a presented not-entered information candidate selection unit configured to select a plurality of pieces of not-entered information associated with the image feature amount from not-entered information that is medical information other than the entered information as presented not-entered information candidates that are candidates for presentation;
a processor configured to acquire an inference result using the entered information and each of the presented not-entered information candidates, wherein the presented not-entered information selected by the presented not-entered information candidate selection unit includes not-entered information that denies a predicted diagnosis name.

2. The medical diagnostic supporting apparatus according to claim 1, further comprising:
  a presented not-entered information selection unit configured to select presented not-entered information from the presented not-entered information candidates based on the inference result;
  a presentation unit configured to present the presented not-entered information selected by the presented not-entered information selection unit.

3. The medical diagnostic supporting apparatus according to claim 2, wherein the presented not-entered information selected by the presented not-entered information selection unit includes not-entered information that denies a predicted diagnosis name.

4. The medical diagnostic supporting apparatus according to claim 1, wherein the presented not-entered information candidate selection unit selects the presented not-entered information from the presented not-entered information candidates based on the plurality of inference results such that the not-entered information that denies the predicted diagnosis name has the lowest inferred probability out of the plurality of inference results.

5. The medical diagnostic supporting apparatus according to claim 2,
  wherein the processor acquires a plurality of inference results using the entered information and each of the presented not-entered information candidates, and
  wherein the presented not-entered information candidate selection unit selects the plurality of pieces of not-entered information from the not-entered information based on the plurality of inference results such that the not-entered information that denies a predicted diagnosis name has the lowest inferred probability out of the plurality of inference results.

6. The medical diagnostic supporting apparatus according to claim 2, wherein the processor acquires probability belonging to a diagnosis name based on the entered information as an input with use of a probabilistic inference model.

7. The medical diagnostic supporting apparatus according to claim 6, wherein the probabilistic inference model is a model expressing a phenomenon by a causal relationship between a plurality of events.

8. The medical diagnostic supporting apparatus according to claim 1, wherein the not-entered information is medical information corresponding to the image feature amount based on the medical image.

9. A method for providing information for supporting a medical diagnosis, the method comprising:
  inputting a medical image that is a target of the medical diagnosis;
  acquiring one or more pieces of medical information relating to the medical image as entered information;
  acquiring an image feature amount from the medical image;
  selecting a plurality of pieces of not-entered information associated with the image feature amount from not-entered information that is medical information other than the entered information as presented not-entered information candidates that are candidates for presentation, and
  acquiring, using a processor, an inference result using the entered information and each of the presented not-entered information candidates,
  wherein the presented not-entered information selected by the selecting step includes not-entered information that denies a predicted diagnosis name.

10. A non-transitory computer-readable storage medium storing a computer program for causing a computer to function as a medical diagnostic supporting apparatus for providing information which supports a medical diagnosis, the medical diagnostic supporting apparatus comprising:
  a medical image input unit configured to input a medical image that is a target of the medical diagnosis;
  a medical information acquisition unit configured to acquire one or more pieces of medical information relating to the medical image as entered information;
  an image feature amount acquisition unit configured to acquire an image feature amount from the medical image; and
  a presented not-entered information candidate selection unit configured to select a plurality of pieces of not-entered information associated with the image feature amount from not-entered information that is medical information other than the entered information as presented not-entered information candidates that are candidates for presentation;
  a processor configured to acquire an inference result using the entered information and each of the presented not-entered information candidates,
  wherein the presented not-entered information selected by the presented not-entered information candidate selection unit includes not-entered information that denies a predicted diagnosis name.

11. A medical diagnostic supporting apparatus for displaying information which supports a medical diagnosis, the medical diagnostic supporting apparatus comprising:
  an image acquisition unit configured to acquire a medical image that is a target of medical diagnosis;
  an information acquisition unit configured to acquire a piece of entered information corresponding to one of pieces of medical information, the entered information related to the medical image, entered for the medical diagnosis, and defining a state for the one of the pieces of medical information;
  a feature amount acquisition unit configured to acquire a feature amount from the medical image;
  a selection unit configured to select a piece of not-entered information that is not entered about the medical image based on the feature amount of the medical image, the selected piece of not-entered information corresponding to one of the pieces of medical information which does not correspond to the acquired entered information; and
  a display control unit configured to cause a display unit to display the selected not-entered information.

12. The medical diagnostic supporting apparatus according to claim 11, wherein the selection unit is configured to identify pieces of not-entered information about the medical image based on observation from image interpretation inputted about the medical image and to select the pieces of not-entered information related to image observation to be inputted about the medical image from the identified pieces of not-entered information.

13. The medical diagnostic supporting apparatus according to claim 11, further comprising:
  an observation acquisition unit configured to acquire the observation from image interpretation inputted about the medical image; and
  an inference unit configured to infer a disease condition of the medical image based on the inputted observation from image interpretation, wherein the selection unit is configured to select the piece of not-entered information to be displayed from pieces of not-entered information based on the inputted observation from image interpretation and the inferred disease condition.

14. The medical diagnostic supporting apparatus according to claim 11, further comprising: an identification unit configured to identify at least one piece of not-entered information corresponding to the feature amount.

15. The medical diagnostic supporting apparatus according to claim 11, further comprising:
a memory configured to store a group of inputtable observation from image interpretation; and
an identification unit configured to identify observation from image interpretation corresponding to the feature amount from the inputtable observation from image interpretation based on the feature amount.

16. The medical diagnostic supporting apparatus according to claim 11, further comprising:
an observation acquisition unit configured to acquire the observation from image interpretation inputted about the medical image; and
an inference unit configured to infer a disease condition of the medical image based on the inputted observation from image interpretation,
wherein the selection unit is configured to identify pieces of not-entered information about the medical image based on the observation from image interpretation inputted about the medical image, and to select one of the identified pieces of not-entered information based on a degree of influence of inputting each of the identified pieces of the identified not-entered information on an inference result of the disease condition of the medical image by the inference unit.

17. The medical diagnostic supporting apparatus according to claim 16, wherein the selection unit is configured to select the piece of not-entered information having a greatest degree of influence.

18. The medical diagnostic supporting apparatus according to claim 16,
wherein the inference unit is configured to acquire a plurality of disease condition candidates and an inference probability of each disease condition, and
wherein the selection unit is configured to select the piece of not-entered information for each of the plurality of disease condition candidates.

19. The medical diagnostic supporting apparatus according to claim 16, further comprising: an observation acquisition unit configured to acquire observation from image interpretation about the medical image based on an input operation from an operation unit.

20. A medical diagnostic supporting system for displaying information which supports a medical diagnosis, the medical diagnostic supporting apparatus comprising:
an image acquisition unit configured to acquire a medical image that is a target of medical diagnosis;
an information acquisition unit configured to acquire a piece of entered information corresponding to one of pieces of medical information, the entered information related to the medical image, entered for the medical diagnosis, and defining a state for the one of pieces of medical information;
a feature amount acquisition unit configured to acquire a feature amount from the medical image;
a selection unit configured to select a pieces of not-entered information that is not entered about the medical image based on the feature amount of the medical image, the selected piece of not-entered information corresponding to one of the pieces of medical information which does not correspond to the acquired entered information; and
a display control unit configured to cause a display unit to display the selected not-entered information.

21. A display control method for displaying information which supports a medical diagnosis, the display control method comprising:
acquiring a medical image that is a target of medical diagnosis;
acquiring a piece of entered information corresponding to one of pieces of medical information, the entered information related to the medical image, entered for the medical diagnosis, and defining a state for the one of the pieces of medical information;
acquiring a feature amount from the medical image;
selecting a pieces of not-entered information that is not entered about the medical image based on the feature amount of the medical image, the selected piece of not-entered information corresponding to one of the pieces of medical information which does not correspond to the acquired entered information; and
causing a display unit to display the selected not-entered information.

22. A non-transitory computer-readable storage medium storing a computer program for causing a computer to execute the display control method according to claim 21.

* * * * *